United States Patent [19]

Lürssen

[11] Patent Number: 4,765,823
[45] Date of Patent: Aug. 23, 1988

[54] AGENT FOR REGULATING PLANT GROWTH

[75] Inventor: Klaus Lürssen, Berg.-Gladbach, Fed. Rep. of Germany

[73] Assignee: Bayer Aktiengesellschaft, Leverkusen, Fed. Rep. of Germany

[21] Appl. No.: 818,529

[22] Filed: Jan. 12, 1986

[30] Foreign Application Priority Data

Jan. 22, 1985 [DE] Fed. Rep. of Germany ....... 3501856

[51] Int. Cl.$^4$ ............................................. A01N 43/64
[52] U.S. Cl. ........................................... 71/92; 71/96; 71/121
[58] Field of Search ............................ 71/96, 92, 121

[56] References Cited

U.S. PATENT DOCUMENTS 3,156,554  11/1964  Tolbert .................................. 71/121
4,452,625  6/1984  Hurssen et al. ........................ 71/76

FOREIGN PATENT DOCUMENTS 0005600  11/1979  European Pat. Off. .
0015387  9/1980  European Pat. Off. .
0057357  8/1982  European Pat. Off. .
0127944  12/1984  European Pat. Off. .
2081700  2/1986  United Kingdom .

OTHER PUBLICATIONS

Research Disclosure, No. 176 (1978), pp. 44–47.

Primary Examiner—Catherine L. Mills
Attorney, Agent, or Firm—Sprung, Horn, Kramer & Woods

[57] ABSTRACT

A method of regulating the growth of plants which comprises applying to such plants or to a locus in which said plants are grown a plant growth-regulating effective amount of a composition comprising (a) 1-cyclohexyl-4,4-dimethyl-2-(1,2,4-triazol-1-yl)-pent-1-en-3-ol of the formula

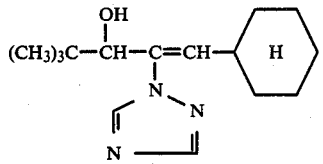

and (b) 2-chloroethyl-trimethyl-ammonium chloride of the formula

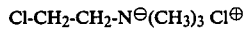

5 Claims, No Drawings

AGENT FOR REGULATING PLANT GROWTH

The present invention relates to new active compound combinations which consist of the known 1-cyclohexyl-4,4-dimethyl-2-(1,2,4-triazol-1-yl)-pent-1-en-3-ol, on the one hand, and the known 2-chloroethyl-trimethylammonium chloride, on the other hand, and are very suitable for regulating plant growth.

It has already been disclosed that 1-cyclohexyl-4,4-dimethyl-2-(1,2,4-triazol-1-yl)-pent-1-en-3-ol possesses plant growth-regulating properties (compare European Published Application 0,015,387). The activity of this compound is good; however, in the case of certain indications it leaves something to be desired, if low amounts are used.

Further, it is already known that 2-chloroethyltrimethylammonium chloride may be employed to regulate plant growth (compare U.S. Pat. Specification No. 3,156,554). However, the activity of this compound is not always satisfactory if low amounts are used.

It has now been found that the new active compound combinations of (a) 1-cyclohexyl-4,4-dimethyl-2-(1,2,4-triazol-1-yl)-pent1-en-3-ol of the formula

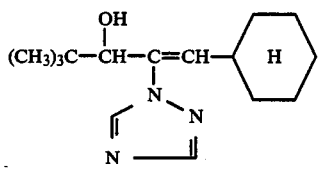

(I)

and N (b) 2-chloroethyl-trimethyl-ammonium chloride of the formula

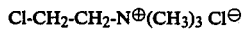  (II)

are very suitable for regulating plant growth.

Surprisingly, the plant growth-regulating activity of the active compound combinations according to the invention is substantially higher than the sum of the effects of the individual active compounds. Accordingly, this is a case of an unforeseeable synergistic effect and not merely of a supplementary effect.

The compound of the formula (I) possesses an asymmetrically substituted carbon atom and can therefore occur in the form of a racemate or in the forms of the two optical isomers. Moreover, the compound of the formula (I) can, depending on the position of the substituents on the C=C double bond, also exist in two geometrical isomeric forms. The invention relates not only to their isomer mixtures but also to the individual isomers. The racemic isomer mixture, and the (-)-antipode of (E)-1-cyclohexyl-4,4-dimethyl-3-hydroxy-2-(1,2,4-triazol-1-yl)-pent-1-ene of the formula

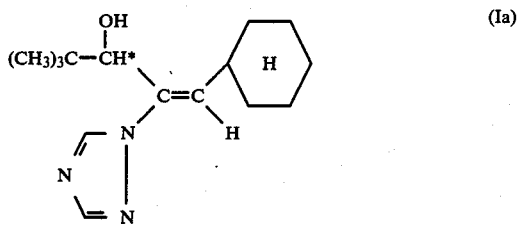 (Ia)

are preferred. The (-)-antipode is here to be understood as the enantiomer which rotates the plane of rotation of linearly polarized light of the sodium D-line to the left.

The active substances contained in the active substance combinations according to the invention are already known (compare European Published Specification No. 0,015,387, DE-OS (German Published Specification) No. 3,301,122 and U.S. Pat. Specification No. 3,156,554).

The synergistic effect manifests itself particularly clearly if the active compounds are present in particular weight ratios in the active compound combinations according to the invention. However, the weight ratios of the active compounds in the active compound combinations can be varied within a relatively wide range. In general, 0.05 to 5 parts by weight, preferably 0.1 to 4 parts by weight, of active compound of the formula (II) are used per part by weight of active compound of the formula (I).

The active compound combinations which can be used according to the invention engage in the metabolism of the plants and can therefore be employed as plant growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound, applied to the plants or their environment and the way in which the compounds are applied. In every case, growth regulators are intended to influence the crop plants in the particular manner desired.

Plant growth regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sports grounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved.

An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compound combinations according to the invention above all show a strong plant growth-inhibiting activity, especially in monocotyledon plants, such as, for example, cereals and grass.

In the present case, cereals are to be understood as all customary types of cereals. These preferentially include oats, rye, barley, wheat and rice.

The active compounds according to the invention can be converted to the customary formulations, such as solutions, emulsions, suspensions, powders and granules.

These formulations are produced in known manner, for example by mixing the active compounds with extenders, that is, liquid solvents and/or solid carriers, optionally with the use of surface-active agents, that is, emulsifying agents and/or dispersing agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products. As dispersing agents there are suitable: for example, lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colourants such as inorganic pigments, for example iron oxide, titanium oxide and Prussian Blue, and organic dyestuffs, such as alizarin dyestuffs azo- and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound combinations according to the invention can be present in the formulations as a mixture with other known active compounds, such as fungicides, insecticides, acaricides and herbicides, and also as mixtures with fertilizers.

The active compound combinations can be used as such, in the form of their formulations or as the use forms prepared therefrom, such as ready-to-use solutions, emulsifiable concentrates, emulsions, suspensions, wettable powders, soluble powders and granules.

They are used in the customary manner, for example by watering, spraying, atomizing, scattering, and the like.

The active compound concentrations can be varied within a substantial range. In general, 0.01 to 50 kg, preferably 0.05 to 10 kg, of the active compound are employed per hectare of soil surface.

As regards the time of application, the rule is that the active compound combinations are applied within a preferred period of time, the exact definition of which depends on the climatic and vegetative circumstances.

The good plant growth-regulating action of the active compound combinations according to the invention can be seen from the examples which follow. While the individual active compounds have weaknesses in growth-regulating action, the combinations show an action which goes beyond a simple additive action.

A synergistic effect exists with growth regulators whenever the growth-regulating action of the active compound combinations is greater than the sum of the actions of the individually applied active compounds.

The action to be expected for a given combination of two plant growth regulators can (compare Colby, S. R., "Calculating synergistic and antagonistic responses of herbicide combinations", Weeds 15, pages 20–22, 1967) be calculated as follows:

If $X=\%$ growth regulation by active compound A used in an amount of p kg/ha, and $Y=\%$ growth regulation by active compound B used in an amount of q kg/ha and $E=$ the expected growth regulation by the active compounds A and B used in amounts of p and q kg/ha, then $E = X + Y - (X \cdot Y)/100$.

If the actual growth inhibition is greater than calculated, the action of the combination is superadditive, that is to say a synergistic effect exists.

The tables in Examples A and B show clearly that the found growth regulating action of the active compound combinations according to the invention is greater than the calculated action, that is to say a synergistic effect exists.

EXAMPLE A

Inhibition of growth in wheat

Solvent: 30 parts by weight of dimethylformamide
Emulsifier: 1 part by weight of polyoxyethylene sorbitan monolaurate To produce a suitable preparation of the racemic active compound of the formula (I), 1 part by weight of this active compound is mixed with the stated amounts of solvent and emulsifier and the mixture is made up to the desired concentration with water.

To produce a suitable preparation of the active compound of the formula (II), a commercial liquid formulation which contains 46 percent by weight of this active compound is made up to the desired concentration with water.

To produce a suitable preparation of an active compound combination according to the invention, 1 part by weight of racemic active compound of the formula (I) is mixed with the stated amounts of solvent and emulsifier, the desired amount of the commercial liquid formulation containing 46 percent by weight of active compound of the formula (II) is added and the mixture is made up to the desired concentration with water.

Wheat plants are grown in a greenhouse, in pots each having a surface area of 100 cm², to the 2-leaf stage. In this stage, the plants are sprayed with the equivalent of 500 litres/ha of the active compound preparation. After 3 weeks, the additional growth of all plants is measured and the inhibition of growth is calculated in percent of the additional growth of the control plants. 100% inhibition of growth means that growth has stopped and 0% means a growth corresponding to that of the control plants.

The active compounds, amounts used and test results are shown in the table which follows.

TABLE A

| | Inhibition of growth in wheat | | |
|---|---|---|---|
| Active compounds or combination | Amount of active compound applied, kg/ha | Inhibition of growth in % found* | calculated* |
| (I) | 0.5 | 21 | — |
| | 1.0 | 35 | — |
| (II) | 0.5 | 50 | — |
| | 1.0 | 59 | — |
| (I) + (II) | 0.25 + 0.25 | 59 | — |
| (I) + (II) | 0.5 + 0.5 | 77 | 60.5 |

*found = found inhibition of growth
*calculated = inhibition of growth calculated from the Colby equation given above

EXAMPLE B

Inhibition of growth in rye

Solvent: 30 parts by weight of dimethylformamide
Emulsifier: 1 part by weight of polyoxyethylene sorbitan monolaurate To produce a suitable preparation of the racemic active compound of the formula (I), 1 part by weight of this active compound is mixed with the stated amounts of solvent and emulsifier and the mixture is made up to the desired concentration with water.

To produce a suitable preparation of the active compound of the formula (II), a commercial liquid formulation which contains 46 percent by weight of this active compound is made up to the desired concentration with water.

To produce a suitable preparation of an active compound combination according to the invention, 1 part by weight of racemic active compound of the formula (I) is mixed with the stated amounts of solvent and emulsifier, the desired amount of the commercial liquid formulation containing 46 percent by weight of active compound of the formula (II) is added and the mixture is made up to the desired concentration with water.

Rye plants are grown in a greenhouse, in pots each having a surface area of 100 cm², to the 2-leaf stage. In this stage, the plants are sprayed with the equivalent of 500 litres/ha of the active compound preparation. After 3 weeks, the additional growth of all plants is measured and the inhibition of growth is calculated in percent of the additional growth of the control plants. 100% inhibition of growth means that growth has stopped and 0% means a growth corresponding to that of the control plants.

The active compounds, amounts used and test results are shown in the table which follows.

TABLE B

| | Inhibition of growth in rye | |
|---|---|---|
| Active compounds or combination | Amount of active compound applied, kg/ha | Inhibition of growth in % |
| (I) | 0.5 | 16 |
| | 1.0 | 25 |
| (II) | 0.5 | 16 |
| | 1.0 | 15 |
| (I) + (II) | 0.25 + 0.25 | 23 |
| (I) + (II) | 0.5 + 0.5 | 30 |

It will be understood that the specification and examples are illustrative but not limitative of the present invention and that other embodiments within the spirit and scope of the invention will suggest themselves to those skilled in the art.

I claim:

1. A plant growth-inhibiting composition comprising a plant growth-regulating effective amount of
    (a) 1-cyclohexyl-4,4-dimethyl-2-(1,2,4-triazol-1-yl)pent-1-en-3-ol of the formula $$(CH_3)_3C-\underset{\underset{\underset{N\diagdown N}{\overset{N}{\diagup}}}{|}}{CH}-C=CH-\langle H \rangle$$

and
    (b) 2-chloroethyl-trimethyl-ammonium chloride of the formula $Cl\text{-}CH_2\text{-}CH_2\text{-}N^{\oplus}(CH_3)_3\ Cl^{\ominus}$ in 0.1 to 4 times the weight of (a).

2. A method of inhibiting the growth of plants which comprises applying to such plants or to a locus in which said plants are grown a plant growth-inhibiting effective amount of a composition according to claim 1.

3. The method according to claim 2, wherein the total amount of the active ingredients is between 0.01 and 50 kg per hectare.

4. The method according to claim 2, wherein the total amount of the active ingredients is between 0.05 and 10 kg per hectare.

5. The method according to claim 2, wherein the composition is applied to cereals or to a field in which cereals are growing or to be grown.

* * * * *

UNITED STATES PATENT AND TRADEMARK OFFICE
CERTIFICATE OF CORRECTION

PATENT NO. : 4,765,823
DATED : Aug. 23, 1988
INVENTOR(S) : Lürssen

It is certified that error appears in the above-identified patent and that said Letters Patent is hereby corrected as shown below:

| | |
|---|---|
| Title Page, under "U.S. Patent Documents", line 2 | Delete "Hurssen" and substitute --Lürssen-- |
| Title Page, under "ABSTRACT", Last line | Correct formula to $--Cl-CH_2-CH_2-N^{\oplus}(CH_3)_3 Cl^{\ominus}--$ |

Signed and Sealed this

Sixth Day of June, 1989

Attest:

DONALD J. QUIGG

Attesting Officer

Commissioner of Patents and Trademarks